United States Patent [19]

Jarvis, Jr.

[11] Patent Number: 4,803,168

[45] Date of Patent: Feb. 7, 1989

[54] MICROENCAPSULATION WITH POLYMERS

[75] Inventor: Allan P. Jarvis, Jr., Newburyport, Mass.

[73] Assignee: Damon Biotech, Inc., Needham Heights, Mass.

[21] Appl. No.: 873,283

[22] Filed: Jun. 4, 1986

Related U.S. Application Data

[63] Continuation of Ser. No. 528,395, Sep. 1, 1983, abandoned.

[51] Int. Cl.$^4$ ............................................. C12N 5/00
[52] U.S. Cl. .................... 435/240.22; 435/1; 435/178; 264/4; 935/54; 424/422; 424/424; 424/425
[58] Field of Search ............ 424/31, 32, 34, 35, 424/94, 101, 106, 110, DIG. 7; 435/1, 174, 175, 177, 178, 182, 188, 240, 240.22; 264/4; 3/1; 935/54

[56] References Cited

U.S. PATENT DOCUMENTS

| 4,301,067 | 11/1981 | Koshugi . | |
|---|---|---|---|
| 4,322,311 | 3/1982 | Lim et al. | 424/DIG. 7 X |
| 4,324,683 | 4/1982 | Lim et al. | 424/32 X |
| 4,352,883 | 10/1982 | Lim | 435/178 |
| 4,391,909 | 7/1983 | Lim | 264/4 X |
| 4,407,957 | 10/1983 | Lim | 435/178 |
| 4,409,331 | 10/1983 | Lim | 435/178 |
| 4,501,835 | 2/1985 | Berke | 424/DIG. 7 X |

FOREIGN PATENT DOCUMENTS 3005633 8/1981 Fed. Rep. of Germany ...... 435/182
55-102436 8/1980 Japan .

OTHER PUBLICATIONS

Muzzarelli-Chitin, Permagon Press (1977) pp. 69 & 257.
Kikuchi et al.-Die Makromolekulare Chemie vol. 175 (1974) pp. 3593-3596.
Fukuda-Bull. Chem. Soc. Japan vol. 53 (1980) pp. 837-840.
K. D. Vorlop et al. "Formation of Spherical Chitosan Viocatalysts by Ionotropic Gelation", Biotechnology Letters, vol. 3, No. 1, pp. 9-14 (1981).

Primary Examiner—Sam Rosen
Attorney, Agent, or Firm—Lahive & Cockfield

[57] ABSTRACT

Disclosed is a process for damage-free encapsulation of a variety of core materials including viable cells. The core material is suspended in an aqueous solution of a polymeric material containing cationic groups such as an aminated glucopolysaccharide, e.g. chitosan. A temporary matrix is formed by gelling droplets of the suspension with a divalent or multivalent anion. The temporary matrix is permanently cross-linked with a polymeric material containing plural anionic groups, e.g., polyaspartic or polyglutamic acid, to form a semipermeable membrane. The interior of the microcapsule may be resolublized by subjecting the capsule to a solution of low molecular weight cations. The process produces microcapsules which are not sticky, do not clump and allow viable cell growth and proliferation.

6 Claims, No Drawings

4,803,168

MICROENCAPSULATION WITH POLYMERS

This application is a continuation of application Ser. No. 528,395, filed Sept. 1, 1983, now abandoned.

BACKGROUND OF THE INVENTION

This invention relates to the encapsulation of core material within a semipermeable membrane. More particularly, the invention relates to a process for encapsulating pH, temperature, or ionic strength-sensitive core material, including viable cells, within a microcapsule. The encapsulation process disclosed herein allows formation of a semipermeable membrane without damaging the core material. The invention also relates to a capsule having an aminated polymeric inner layer ionically bound to an anionic polymeric outer layer.

Although a number of processes for microencapsulation of core material have been developed, most of these processes can not be used for pH, temperature or ionic strength-sensitive material such as viable cells because of the harsh conditions necessary for encapsulation. U.S. Pat. No. 4,352,883 discloses what is believed to be the first process for successfully encapsulating viable tissue or cells within a semipermeable membrane. In the patented process, a temporary capsule of a gellable material, preferably an anionic gum such as sodium alginate, is formed about the tissue or cells and a permanent, semipermeable membrane is formed by cross-linking surface layers of the temporary capsule. Specifically, a mixture of the gum and the core material is subjected to a gelling solution, preferably a calcium ion solution, to produce a temporary capsule. The resulting temporary capsule is reacted with a solution of a polycationic material to form a permanent membrane. The interior of the capsule may be reliquified by reestablishing conditions under which the anionic gum is liquid, e.g., changing the ionic environment by placing the capsules in phosphate buffered saline. Reliquification of the interior of the capsule facilitates nutrient transport across the membrane, promoting cell growth. The process need not damage the core material or hamper the viability of cells because the temperature, ionic strength, and pH ranges used in the encapsulation process need not be harsh.

Accordingly, an object of the invention is to provide a process for encapsulating viable cells or other fragile material in semipermeable membranes. Another object is to provide a process for encapsulating core materials which are difficult to capsulate using known procedures because of pH, ionic strength, charge, or temperature sensitivity. A further object of the invention is to provide an improved capsule comprising a semipermeable membrane. These and other objects and features of the invention will be apparent from the following description.

SUMMARY OF THE INVENTION

In one aspect, the invention features a process for encapsulating core material such as enzymes, antibodies, hormones, or viable cells, e.g., tissue culture or genetically modified cells, within a semipermeable membrane. The core material is suspended in an aqueous medium having dissolved therein a polysaccharide containing cationic groups, preferably an aminated polysaccharide such as poly D Glucosamine (chitosan). A droplet of the suspension is gelled by subjecting the droplet to a solution of a divalent or multivalent anions, e.g., $PO_4^=$, $HPO_4^=$, or $SO_4^=$ salts. A permanent membrane is formed by cross-linking surface layers of the temporary matrix with a polymer containing anionic, preferably carboxyl groups reactive with the cationic groups of the matrix. Poly-L-glutamic acid and poly-L-aspartic acid, either as acids or salts, are preferred anionic polymers. The interior of the capsule may be resolublized by subjecting the capsule to a solution of low molecular weight polycations, e.g., spermadine, spermine, or urea. Reliquification of the interior promotes mass transport between the extracapsular fluid and the intracapsular volume.

In another aspect, the invention features a process for encapsulating a viable cell within a semipermeable membrane. The cell is suspended in an aqueous medium compatable with its viability containing an aminated glucopolysaccharide. A droplet of the suspension is subjected to a gelling solution thereby forming a shape-retaining, water-insoluble temporary matrix. The gelling solution is an aqueous solution of a di or multivalent anions, e.g., phosphate, monohydric phosphate, or sulfate salts. Surface layers of the temporary matrix are permanently crosslinked by subjecting the capsule to a polymer containing a plurality of carboxyl groups, e.g., polyglutamic acid or polyaspartic acid. The interior of the capsule is reliquified in a substantially precipitant-free reaction by subjecting the capsule to a solution of a low molecular weight polycation, e.g., spermadine, spermine, or urea. Reliquification occurs by removal of multivalent anions from the interior gel. Mammalian tissue cells in a tissue growth medium and genetically modified prokaryotic or eukaryotic cells in a growth medium may be encapsulated by this process. The encapsulation procedure is gentle so the encapsulated cell is not damaged and can undergo normal metabolic processes including growth and reproduction within the capsule.

In a further aspect, the invention features a capsule having a membrane defining an enclosed intracapsular volume. The membrane has an inner layer of a polyaminated polymer, preferably an aminated polysaccharide, most preferably an aminated glucopolysaccharide, ionically cross-linked to an outer layer of a polyanionic polymer, preferably a polycarboxylated polymer such as polyglutamic acid or polyaspartic acid, to form a water-insoluble permanent capsule. A cell, preferably a eukaryotic, bacterial, or genetically modified cell, may be disposed within the intracellular volume. If a cell is disposed within the intracellular volume, the polyanionic and polyaminated polymers should be physiologically compatible with the cell.

DESCRIPTION OF THE PREFERRED EMBODIMENT

The present invention provides a process for encapsulating core materials such as viable eukaryotic or prokaryotic, naturally occurring or genetically modified, cells or tissue culture within a semipermeable membrane. The invention also provides a new type of multi-layer capsule.

A gel or temporary matrix is formed about the core material or viable cell by reacting a polysaccharide or glucopolysaccharide containing cationic groups with a multivalent anion. Surface layers of the resulting temporary matrix are ionically cross-linked by a polymer containing anionic, preferably carboxyl, groups forming a permanent membrane encapsulating the core material. The interior of the capsule may be reliquified by subjecting the capsule to a solution of low molecular weight polycations.

Core material, for example, enzymes, hormones, antibodies or viable cells, is suspended in an aqueous medium containing a gellable, cationic group-containing polymer. The preferred gellable polymer is an aminated glucopolysaccharide, most preferably chitosan (poly-D-glucosamine). Chitosan is formed by acid hydrolysis of chitin (poly-D-N-acetylglucosamine), the primary building material of invertebrate exoskeletons. Chitosan is a long chain, aminated polymer which is physiologically compatible with most cells. It is only slightly soluble in water but can be readily dissolved in dilute acetic acid.

Stock solutions of chitosan are prepared by dissolving the chitosan in 0.5 molar acetic acid. The acetic acid is removed from the solution by repeated dialysis against phosphate buffered saline (PBS). Chitosan does not precipitate out of this solution if the solution is kept below 37° C. The preferred stock solution, 1.4% chitosan in PBS, has been stored successfully at 4° C. for extended periods.

Chitosan prepared as described above is mixed with the material to be encapsulated, forming a solution or slurry, before it is formed into droplets or other shapes. Although solutions having a final chitosan concentration of 0.4% (w/v) will gel, optimum gelling is obtained with 0.8-1.2% (w/v) chitosan in isotonic, 125 mM $Na_2HPO_4$. Droplets of the chitosan/core material suspension can be formed by any conventional droplet-forming apparatus. One such droplet-forming apparatus is described below.

A tube containing the suspension is fitted with a stopper which holds a droplet-forming apparatus. The apparatus consists of a housing having an upper air intake nozzle and an elongate hollow body friction fitted into the stopper. A 10 cc syringe equipped with a stepping pump is mounted atop the housing with a needle, e.g., a 0.01 inch I.D. Teflon coated needle, passing through the length of the housing. The interior of the housing is designed such that the tip of the needle is subjected to a constant laminar air flow which acts as an air knife. In use, the stepping pump is actuated to incrementally force droplets of solution from the tip of the needle. Each drop is "cut off" by the air stream and falls approximately 2.5 cm into the gelling solution, preferably a disodium hydrogen phosphate solution, where it is immediately gelled by reaction with the negative ions. The distance between the tip of the needle and the surface of the gelling solution is preferable great enough to allow the chitosan/core material suspension to assume the most physically favorable shape; a sphere (maximum volume for a minimum surface area). Air from the tube bleeds through an opening in the stopper. This procedure results in a "cross-linking" of the gel and the formation of a high viscosity shape-retaining protective temporary matrix containing the suspended core material and its medium. The temporary matrices collect in the solution as a separate phase and may be separated by aspiration.

The preferred multivalent gelling solution is a 125 mM $NaHPO_4$ solution; however, monobasic sodium phosphate and sodium sulfate solutions have also produced acceptable temporary matrices. Sodium citrate can gel the suspension but best results are obtained with monobasic or dibasic phosphate and sulfate solutions. If the anion level is too low (e.g., below approximately 100 mM), gelling may not occur.

Temporary matrices formed by this process are collected and washed to remove excess gelling solution. The matrices are then subjected to a coating or cross-linking solution of a polyanionic, preferably polycarboxylated polymer. A preferred cross-linking solution is a 1% solution of poly-L-aspartic acid or poly-L-glutamic acid, diluted 1:15 with 150 mM sodium chloride yielding a final polymer concentration of $6.6 \times 10^{-4}$ g/100 ml. The molecular weight of the poly-L-aspartic or poly-L-glutamic acid can range from 3,000-100,000 daltons or higher, but the 25,000-60,000 dalton range is preferred. A reaction time of 3-6 minutes at ambient room temperature has been found to be satisfactory.

The following non-limiting examples set forth exemplary procedures for practice of the invention.

EXAMPLE 1

A stock solution of 1.4% chitosan (CSN-Sigma Chemical Co.) in 14-17 mM (w/v) isotonic PBS, prepared as previously described, was used in this experiment. Different concentrations of CSN were tested to determine the optimum CSN concentration for temporary matrix formation. In each case, 1 ml samples were formed from the CSN stock solution and fetal calf serum (FCS-Flow Laboratories). Droplets were produced and introduced into solutions as described below using a droplet-forming apparatus as previously described. Table 1 illustrates three different CSN concentrations (w/v) tested in this experiment, 0.6%, 0.8%, and 1%.

TABLE 1

| Sample # | CSN ml | FCS ml | Concentration CSN (w/v) |
|---|---|---|---|
| 1 | 0.57 | 0.43 | 0.8% |
| 2 | 0.42 | 0.58 | 0.6% |
| 3 | 0.72 | 0.28 | 1.0% |

Two gelling buffers were prepared, 110 mM sodium citrate (Sigma), and 125 mM disodium hydrogenphosphate (Sigma). In all cases, the temporary matrices formed using these buffered solutions were acceptable, but the sodium citrate buffer produced inadequate gelling of sample No. 1. While all of the samples formed acceptable temporary matrices in the disodium hydrogen phosphate buffer, sample 3 provided the best gelling.

A 1% solution of poly-L-aspartic acid (40,000 dalton molecular weight-Sigma), was diluted 1:15 with 150 mM sodium chloride (Sigma) to form a $6.6 \times 10^{-4}$ g/100 ml solution. Temporary matrices formed from sample 3 were removed from the gelling buffer, washed repeatedly with isotonic PBS, and resuspended in the poly-L-aspartic acid solution. After six minutes at room temperature in the poly-L-aspartic acid solution, the cross-linking reaction was complete, forming the permanent membranes. The capsules were substantially spherical, about 380-480 microns in diameter. Some capsules had small tails. Capsules formed by this process were not sticky and had no tendency towards clumping. Porosity of the capsules was determined empirically to be about 80,000 daltons. This example illustrates that acceptable capsules can be formed using the process of this invention.

EXAMPLE 2

This example was conducted to demonstrate that the viability of cells is not impaired by the encapsulation process. The cell culture used in this experiment was the Friend Erythroleukemic cell line (FEL$_{745}$), a mouse erythroleukemic line which grows readily in a suspension culture.

A culture of FEL$_{745}$ cells was centrifuged for 5 minutes and the resulting pellet was resuspended as a slurry in fetal calf serum (Flow Labs). A stock solution of 1.4% chitosan was prepared as previously described and mixed with the cell culture solution, yielding a final chitosan concentration of 1% (w/v) and a cell concentration of about $5 \times 10^6$ cells/ml. Temporary matrices were produced by forcing the chitosan-cell mixture through a droplet-forming apparatus (previously described) and contacting the resulting liquid microspheres with the 125 mM (w/v) phosphate ion solution previously described. The resulting temporary matrices were washed repeatedly with isotonic PBS and resuspended in a $6.6 \times 10^{-4}$ g/100 ml (w/v) solution of poly-L-aspartic acid (40,000 daltons molecular weight) in 150 mM sodium chloride. After six minutes at room temperature in the poly-L-aspartic acid solution, the resulting capsules were washed twice with the culture medium RPMI-1640 (Flow Labs) containing 10% fetal calf serum and antibiotics. The microcapsules were placed into tissue culture flasks with the culture medium and incubated at 37° C.O at a 5% CO$_2$ atmosphere.

Samples of the cell culture were removed at various intervals. Examination under a microscope showed that the cells were growing and reproducing, illustrating cell viability after the encapsulation procedure. As may be noted, there was no reliquification step used since Friend cells can grow in a gel culture as well as a suspension culture. However, many types of cells need a fluid culture to reproduce. Cell viability should not be affected by the resolublization of the capsule interiors. The capsule provides a microenvironment free from external contamination.

Those skilled in the art may find other variations or embodiments of the process and product described herein within the scope of the invention. Acordingly, other embodiments are within the following claims.

What is claimed is:

1. A viable cell-containing capsule comprising a semipermeable membrane defining an enclosed intracapsular volume in which viable mammalian cells are disposed within a culture medium, said membrane consisting essentially of an inner layer comprising chitosan and an outer layer comprising a polyanionic polymer, said chitosan layer and polyanionic polymer being cross-linked by ionic interaction between cationic amine groups on said chitosan and anionic groups on said polyanionic polymer to form a water-insoluble permanent capsule, said encapsulated viable cells being capable of growth and reproduction within said capsule.

2. The capsule of claim 1 wherein said polyanionic polymer is a polycarboxylated polymer.

3. The capsule of claim 2 wherein said polyanionic polymer is polyaspartic acid or a salt thereof.

4. The capsule of claim 2 wherein said polyanionic polymer is polyglutamic acid or a salt thereof.

5. The capsule of claim 1 wherein said chitosan layer and said polyanionic polymer are physiologically compatible with said cell.

6. The capsule of claim 1 wherein said cell comprises a genetically modified cell.

* * * * *